United States Patent
Yang

(10) Patent No.: US 10,599,986 B2
(45) Date of Patent: Mar. 24, 2020

(54) AUXILIARY ANALYSIS SYSTEM USING EXPERT INFORMATION AND METHOD THEREOF

(71) Applicant: kiddeveloping Co., Ltd., Taipei (TW)

(72) Inventor: Yu Ying Yang, Taipei (TW)

(73) Assignee: KIDDEVELOPING CO., LTD., Taipei (TW)

( * ) Notice: Subject to any disclaimer, the term of this patent is extended or adjusted under 35 U.S.C. 154(b) by 1021 days.

(21) Appl. No.: 14/726,527

(22) Filed: May 30, 2015

(65) Prior Publication Data

US 2015/0262065 A1 Sep. 17, 2015

(30) Foreign Application Priority Data

May 30, 2014 (TW) .............................. 103119003 A

(51) Int. Cl.
*G06F 17/00* (2019.01)
*G06N 5/04* (2006.01)
*G06Q 50/20* (2012.01)
*G16H 50/20* (2018.01)

(52) U.S. Cl.
CPC ............ *G06N 5/047* (2013.01); *G06Q 50/20* (2013.01); *G16H 50/20* (2018.01)

(58) Field of Classification Search
CPC ...................................................... G06F 15/18
USPC .............................................. 706/12, 15, 45
See application file for complete search history.

(56) References Cited

U.S. PATENT DOCUMENTS

| | | | |
|---|---|---|---|
| 7,780,595 B2* | 8/2010 | Iliff | G06Q 50/22 600/300 |
| 8,019,582 B2* | 9/2011 | Iliff | G06Q 50/22 703/11 |
| 2003/0014326 A1* | 1/2003 | Ben-Meir | G06Q 30/0611 705/26.3 |
| 2003/0130994 A1* | 7/2003 | Singh | G06F 16/9535 |
| 2004/0024739 A1* | 2/2004 | Copperman | G06F 17/30616 |
| 2007/0173733 A1 | 7/2007 | Le et al. | |
| 2008/0077570 A1* | 3/2008 | Tang | G06F 17/30684 |
| 2008/0140616 A1* | 6/2008 | Encina | G06F 17/30613 |

(Continued)

FOREIGN PATENT DOCUMENTS

| | | |
|---|---|---|
| CN | 1516561 | 7/2004 |
| CN | 1877588 | 12/2006 |
| JP | 2005182738 | 7/2005 |

(Continued)

OTHER PUBLICATIONS

Meiling Zhang, Research on College Students' Psychological Consultation Expert System Based on Weighted Fuzzy Reasoning.

*Primary Examiner* — David R Vincent
(74) *Attorney, Agent, or Firm* — Raymond Y. Chan; David and Raymond Patent Firm

(57) ABSTRACT

An auxiliary analysis system using expert information comprises a user interface and a determination module. The user interface includes a plurality of analysis items which can be triggered by a user. The determination module coupled with the user interface includes a plurality of preliminary results corresponding to the analysis items. Each of the analysis items corresponds to at least one of the preliminary results. The user selects a plurality of analysis items to generate multiple preliminary results, and the preliminary results further generate a final judgment result by an operation process.

18 Claims, 7 Drawing Sheets

(56) References Cited

U.S. PATENT DOCUMENTS

2010/0070448 A1\* 3/2010 Omoigui ............ H01L 27/1463
    706/47

FOREIGN PATENT DOCUMENTS

| JP | 2005332331 | 12/2005 |
|----|------------|---------|
| JP | 2007226531 | 9/2007  |
| JP | 2013073253 | 4/2013  |
| TW | 200732984  | 9/2007  |
| TW | 201204317  | 2/2012  |

\* cited by examiner

AUXILIARY ANALYSIS SYSTEM USING EXPERT INFORMATION AND METHOD THEREOF

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an auxiliary analysis system and method. More particularly, the present invention relates to an auxiliary analysis system and method using expert information.

Description of Related Arts

Traditionally, professional knowledge in various fields is disseminated by books or taught by proficients. With the advance of technology, the change of social environment or special situations, however, the professional knowledge has to update continuously. The dissemination of knowledge by books or by proficient is unable to assess or solve new problems efficiently. Therefore, it is necessary to revise or update more information through continuous observation or evaluation to different matters by experienced experts so that the professional knowledge is able to apply to the latest actual demand. Moreover, application of professional knowledge usually depends on various situations. Amateurs, who fail to harness theories properly, feel difficult to execute or even make wrong decision because of incorrect classification. When they accumulate enough actual experience, false cases have occurred. Service industries, such as psychological counseling, education, clinical medicine judging, business management, business operation, customer servicing, customer complaint responding, or other jobs requiring expert's knowledge and experience, is influenced by real situation. It is difficult to use the professional knowledge from a set of books to assess or solve problems completely. Experts usually revise or add options or parameters according to their accumulated experience and knowledge in the past. However, the experience only exists in the mind of these experts and becomes tacit knowledge of their service. It takes considerable time to train an expert. Hence, in the case that the number of experts is limited, it is impossible to serve the masses of people simultaneously and assess or solve customer's problems instantly. Especially, famous experts can only serve few people because of high cost and time limitation. Additionally, the experience in expert's mind does not record systemically. Thus, experts may forget considerations or fail to remember some analysis items, judging options or parameters, and they also cannot validate by themselves or by other people whether the judgment is correct or not. Although the experts possess professional experience, the risks of misjudgment still exist due to subjective analysis.

Take the field of child psychoanalysis as an example. Child psychoanalysis is a critical part of education of school-age children. Parents in the modern society often neglect children's feelings due to their heavy workload. In addition, they generally are not familiar with psychology and children do not understand how to express their interior problems. Therefore, parents fail to correctly analyze children's psychological condition correctly and understand their really interior problems. Parents also cannot provide correct discipline and assistance that may cause children's deviant behavior and miss the golden time of behavior correction.

In addition, most teachers in school do not have theoretical or practical background in psychology. They fail to provide correct instructions and assistance under this situation. Teachers not only obtain psychology background, but also accumulate experiences and long-term observations to possess professional knowledge during their career so as to judge and deal with child's behavior instantly.

Because children do not have the abilities to judge their problems or express their ideas by themselves during their growth, observation of children behavior is the most efficient way to analyze child's psychological condition. However, behaviorism involves in a wide variety of behaviors and numerous types of analytic theories. It also evolves over time and changes with external environment so that psychologists and educational experts hold different opinions according to their experience and tacit knowledge which update or renew behavior types and the corresponding behavior analysis. These new and updated observations are not recorded systemically and usually keep in the brains of experienced psychologists or educational experts. Due to complication of the analysis, it is hard for new teachers and parents to learn efficiently and remember the content quickly. Moreover, psychologists and educational experts are asked to response questions rapidly while facing the complex behavior of children, thus merely speculate on the questions by their accumulated experience that may cause errors or omissions of judging options and lead to inaccuracy of analysis, because of the complication of the types of child's external behaviors. The prediction module to evaluate the possible reasons of child's behaviors is often revised to improve accuracy according to the theoretical base and experience of the experts. Nevertheless, the evaluated results are inconsistent due to the effect of the different evaluation methods and difficult to verify the accuracy. Therefore, the evaluated results are not able to be confirmed and accumulated systemically to apply the feedback and revise the evaluation methods or parameters.

As a result, users' demands in the fields require integrated experts' knowledge and experiences. The demands such as faster and more accurate analysis to the reasons behind observable concrete facts, suggestions for revision, auxiliary tools of analysis and record for experts, assistance for expert to build tacit knowledge for repeated verification, correction and extensively repeated use, become necessary and will be solved by the system and the method according to the present invention.

SUMMARY OF THE PRESENT INVENTION

An objective of the present invention is to provide an auxiliary analysis system and method using expert information to solve the problems occurred above.

The auxiliary analysis system using expert information according to the present invention comprises a user interface and a determination module coupled with the user interface. The user interface includes a plurality of analysis items which can be triggered by a user. The determination module includes a plurality of preliminary results corresponding to the analysis items, each of which corresponding to at least one of the preliminary results. A user selects more than one analysis items to generate multiple preliminary results, and the preliminary results further generate a final judgment result by an operation process.

In one embodiment, the operation process includes a weighted process to generate the final judgment result according to the number of the preliminary results corresponding to the analysis items selected by the user.

In another embodiment, each of the preliminary results includes a weighted score and a judgment group, each judgment group corresponding to at least one of the preliminary results, the operation process respectively adding the weighted scores of the preliminary results together of each of the judgment groups and each of the judgment groups correspondingly obtaining a total weighted score.

In yet another embodiment, the operation process ranks the judgment groups by the corresponding total weighted scores.

In yet another embodiment, each of the judgment groups respectively has an attribute defining whether two of the judgment groups conflict with each other, the operation process obtaining a difference between the total weighted scores of judgment groups which conflict with each other, renewing the total weighted score of the judgment group with the higher weighted score according to the difference, removing the judgment group with the lower weighted score, and ranking the remaining judgment groups by the corresponding total weighted scores.

In yet another embodiment, each of the judgment groups respectively has an attribute defining whether two of the judgment groups conflict with each other, the operation process removing the judgment group with lower total weighted score from the judgment groups conflicting with each other, and ranking the remaining judgment groups by the corresponding total weighted scores.

In yet another embodiment, each of the preliminary results has a weighted score and an attribute defining whether two of the preliminary results can be added together, the operation process obtaining a total value by adding the weighted scores of the preliminary results that can be added together, renewing the higher weighted score of the preliminary result according to the total value, removing the preliminary result with the lower weighted score, and ranking the remaining preliminary results by the corresponding weighted scores.

In yet another embodiment, each of the preliminary results has a weighted score and an attribute defining whether two of the preliminary results conflict with each other, the operation process obtaining a difference between the weighted scores that their corresponding preliminary results conflict with each other, renewing the higher weighted score of the preliminary result according to the difference, removing the preliminary result with the lower weighted score, and ranking the remaining preliminary results by the corresponding weighted scores.

In yet another embodiment, each of the preliminary results has a weighted score and an attribute defining whether two of the preliminary results conflict with each other, the operation process removing the preliminary result with the lower weighted score that their corresponding preliminary results conflict with each other, and ranking the remaining preliminary results by the corresponding weighted scores.

In yet another embodiment, each of the analysis items corresponds to at least one analysis judging unit which correspondingly connect to at least one of the preliminary results through a hierarchical structure.

In yet another embodiment, the auxiliary analysis system according to the present invention further comprises an administrator interface coupled with the user interface and the determination module, the administrator interface including a plurality of edition items for editing at least one selected from the analysis items and at least one of the preliminary results of each of the analysis items.

In yet another embodiment, the auxiliary analysis system according to the invention further comprises an administrator interface coupled with the user interface and the determination module, the administrator interface including a plurality of edition items for editing at least one selected from the analysis items, at least one of the preliminary results of each of the analysis items, each of the weighted scores corresponding to each of the preliminary results, each of the judgment groups corresponding to each of the preliminary results, and/or each of the attributes corresponding to each of the judgment groups.

In yet another embodiment, the edition items further apply to edit at least one of the analysis judging units each of which correspondingly connects to at least one of the preliminary results through a hierarchical structure.

In yet another embodiment, the auxiliary analysis system according to the invention further comprises an administrator interface coupled with the user interface and the determination module, the administrator interface including a plurality of edition items for editing at least one selected from the analysis items, at least one of the preliminary results of each of the analysis items, the weighted scores corresponding to the preliminary results, and the attributes corresponding to the preliminary results.

In yet another embodiment, the edition items further apply to edit at least one of the analysis judging units each of which correspondingly connects to at least one of the preliminary results through a hierarchical structure.

The auxiliary analysis method using expert information comprises the steps of: receiving triggers of a plurality of analysis items, each of which corresponds at least one of preset preliminary results; and executing an operation process to generate a final judgment result according to a plurality of the preliminary results of the triggered analysis items.

In one embodiment, the auxiliary analysis method according to the invention further comprises the steps of: receiving a trigger of at least one edition item and obtaining editing information to edit the corresponding analysis item or the corresponding preliminary result; and saving the edited analysis item or the preliminary result.

The invention further provides an auxiliary analysis system using expert information comprising a user interface, an analysis database and an operation processor. The user interface includes a plurality of analysis items which can be triggered by a user. The analysis database includes at least one analysis judging unit corresponding to each of the analysis items and a plurality of preliminary results connected to the analysis judging units. The operation processor coupled to the analysis database to receive a plurality of the preliminary results from the analysis database and generate a final judgment result by an operation process.

In one embodiment, the auxiliary analysis system according to the invention further comprises an administrator interface coupled with the user interface and the analysis database, the administrator interface including a plurality of edition items for editing at least one selected from the analysis items and the preliminary results corresponding to the analysis items.

The auxiliary analysis system and method thereof according to the invention provide a fast and accurate evaluation approach to record, adjust and apply wildly expert information. In the field of child psychoanalysis, parents and teachers easily understand the psychological causes of child behaviors and afford correct discipline, or child psychologists and educational experts are able to apply them as auxiliary reference.

It is to be understood, however, that the foregoing general description and the following detailed embodiment are illustrative only, not to limit the claimed scope of the invention.

BRIEF DESCRIPTION OF THE DRAWINGS

The accompanying drawings are parts of the specification of the invention to illustrate the embodiments of the invention. The drawings along with the detailed description are applied to demonstrate the principle of the invention.

DETAILED DESCRIPTION OF THE PREFERRED EMBODIMENT

Figure 1:
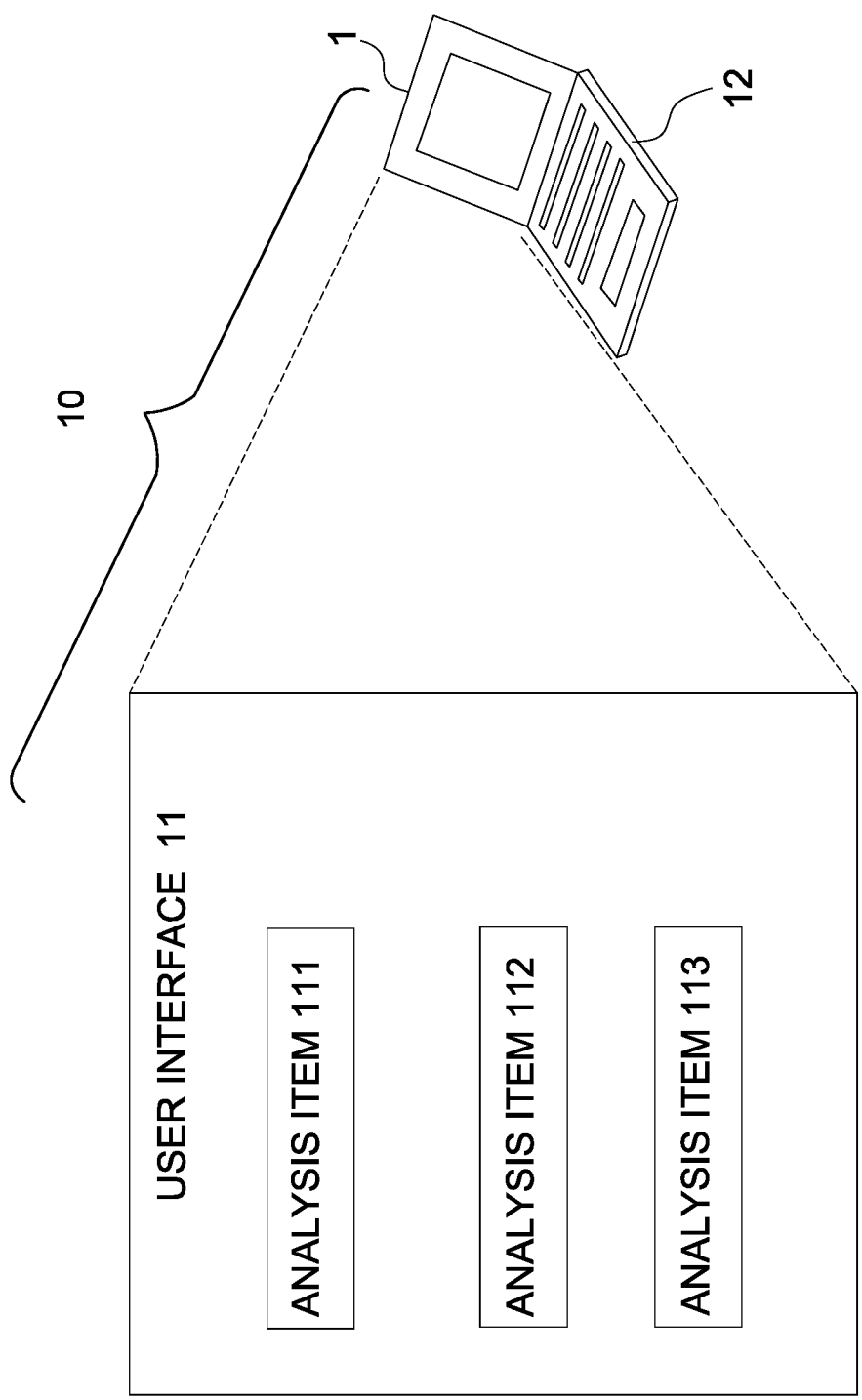
FIG. 1 is a schematic view of the operation screen of a user interface in an embodiment according to the system of the invention.

Please refer to the exemplary embodiments according to the invention, together with the drawings illustrating the exemplary embodiments. In addition, the same or similar elements/components in the drawings and embodiment are applied to represent the same or similar parts.

The following embodiments, expert information includes at least the knowledge that experts obtain from learning or the experience that experts obtain from practical work. When an element is "connected to" or "coupled to" another element, that means the element is directly connected to or coupled to another element, or having an intermediate element between the two elements, or transmission connection of data, or transmission connection of the internet data. The term "module" represents at least one or multiple elements, each of which would be hardware implementation or software implementation.

FIG. 1 is a schematic view of an embodiment according to the system of the invention. In FIG. 1, the auxiliary analysis system 10 using expert information operates in a calculating device 1. In this embodiment, the calculating device 1 is an electric device with a processing unit to calculate data, such as a cloud server, a desktop computer, a laptop computer, a tablet computer, or a smart phone, which is not limited in the invention. The auxiliary analysis system 10 using expert information further includes a user interface 11 and a determination module 12. The user interface 11 includes at least one analysis item 111, 112, 113 which can be triggered by a user. In one of the embodiment according to the invention, the number of the analysis items is 3. But in other embodiment, the number of the analysis items may be 10, which is not limited in the invention. The analysis item is an item which is preset according to the concrete facts (or the concrete behavior facts) in professional books or by expert observations, so that the user can select suitable analysis items to process analysis. In the embodiment, the determination module 12 includes a analysis database 122 and an operation processor 121 coupled to the analysis database 122. The analysis database 122 includes at least one analysis judging unit corresponding to the analysis item 111, 112, 113 and a plurality of preliminary results connected to the analysis judging units. The operation processor 121 receives a plurality of the preliminary results from the analysis database 122 and generates a final judgment result by an operation process.

Take the field of child psychoanalysis as an example. The analysis item 111 would be "to refuse food when mealtime"; the analysis item 112 would be "to take away elder's stuff"; and the analysis item 113 would be "to ask adults to help him for a trifle". In fact, the analysis items 111, 112, 113 are a rank of behavior items that can be observed from concrete behavior facts. The user correspondingly selects the analysis items 111, 112, 113 according to the observation of the behaviors of analysis objects (children). Additionally, the user can select a function item or input a web address and go to an administrator interface 13 which alternatively adds or deletes analysis items or the content corresponding to the analysis items. The administrator interface 13 further sets permission to execute editing process. In the embodiment, the user interface 11 and the administrator interface 13 are software implementation, which are displayed respectively or simultaneously on a display unit of the calculating device 1.

Figure 5:
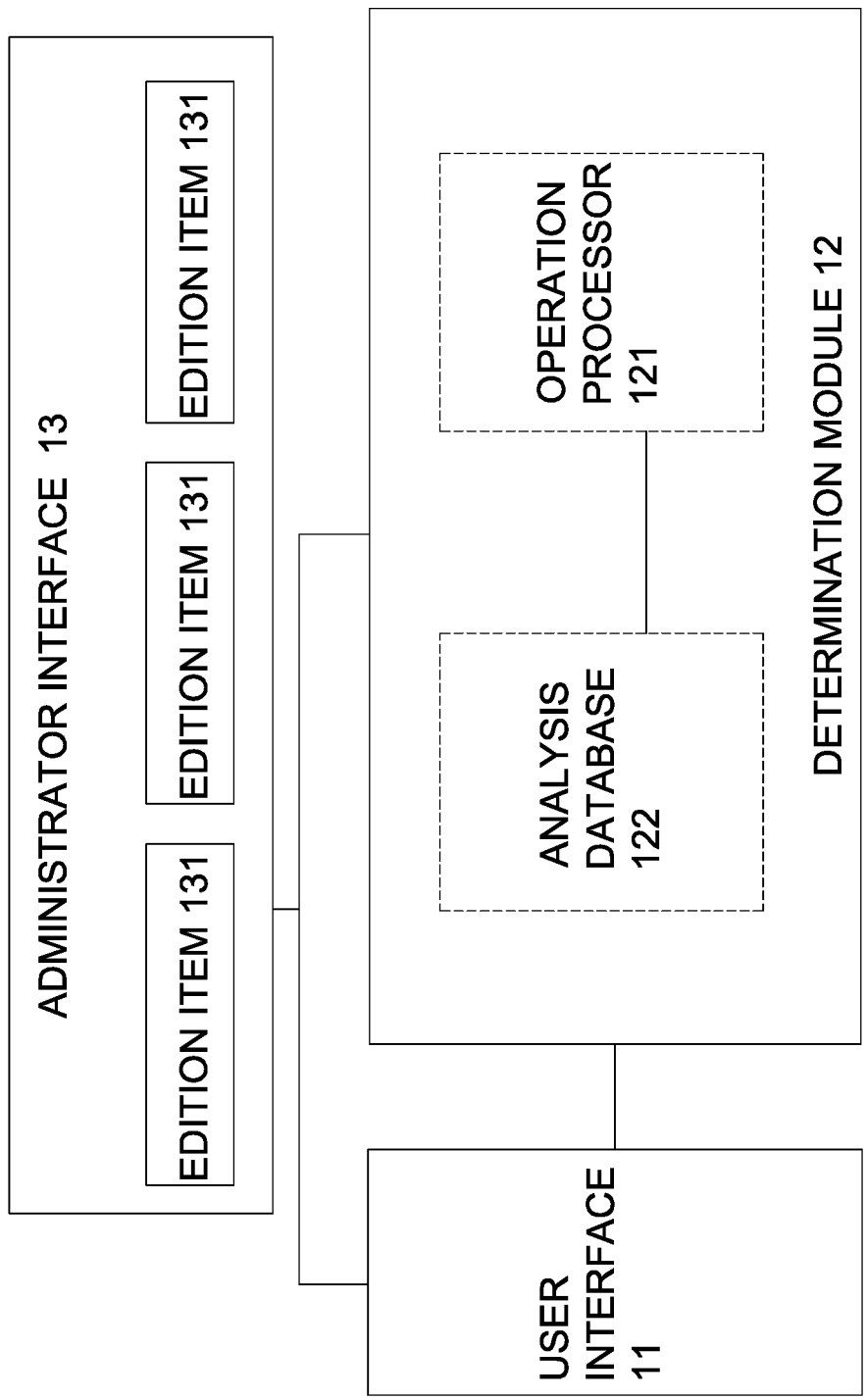
FIG. 5 is a schematic view of the system architecture of an administrator interface in an embodiment according to the system of the invention.

In the embodiment, referring to FIG. 5, the determination module 12 is coupled to the user interface 11 by a data transmitting connection. Besides, the analysis database 122 and the operation processor 121 of the determination module 12 are coupled to the administrator interface 13. The determination module 12 is also coupled to the administrator interface 13 by another data transmitting connection.

The determination module 12 is also installed in the calculating device 1, which could be a laptop computer or a cloud server. When the calculating device 1 is a cloud server, the determination module 12 is installed into the cloud server and applies a transmitting connection of the internet data to enable the user interface 11 and the administrator interface 13 to show on a display unit for users. The display unit could be a display device of an electronic device, such as a smartphone.

Figure 2:
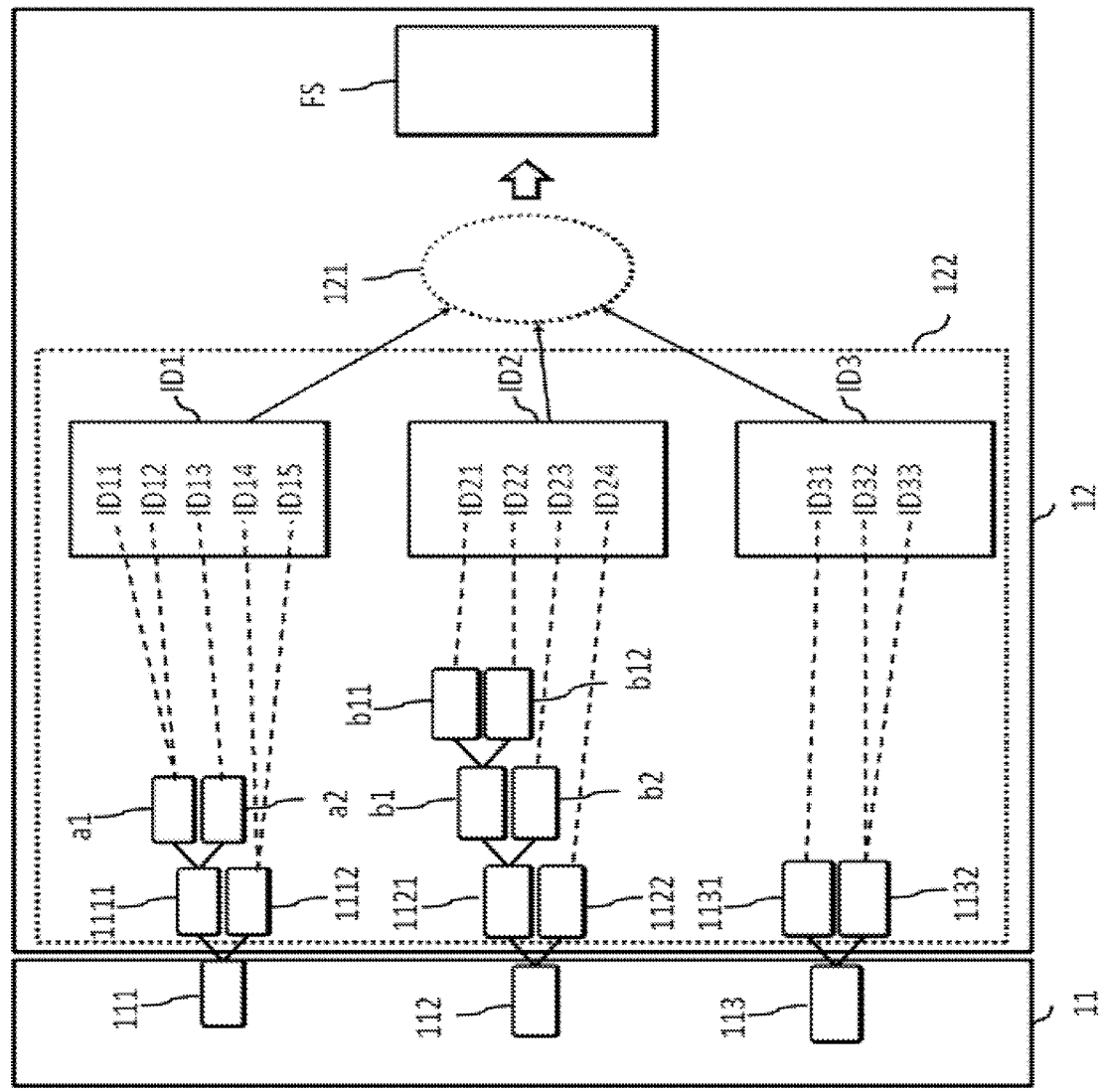
FIG. 2 is a schematic view of the relationship between the internal hierarchy and operation process in a determination module in an embodiment according to the system of the invention.

FIG. 2 is a schematic view of the relationship between the internal hierarchical and operation processor 121 in a determination module 12 in an embodiment according to the system of the invention. Each of the analysis items 111, 112, 113 corresponds to at least one analysis judging unit which correspondingly connects to at least one of the preliminary results through a hierarchical structure. Hence, each of the analysis items 111, 112, 113 corresponds to at least one of the preliminary results. In the embodiment, the analysis database 122 includes the corresponding analysis judging units. For example, the analysis item 111 includes first-order analysis judging units 1111, 1112 correspondingly; wherein, the first-order analysis judging unit 1111 includes second-order analysis judging units a1, a2. The analysis item 112 includes first-order analysis judging units 1121, 1122 correspondingly; wherein, the first-order analysis judging unit 1121 includes second-order analysis judging units b1, b2; wherein, the second-order analysis judging unit b2 includes third-order analysis judging units b11, b12. The analysis item 113 includes first-order analysis judging units 1131, 1132 correspondingly. The development of the foregoing each of the analysis items 111, 112, 113 is mainly to speculate the possible reason of each of the concrete behavior facts. Each order of the analysis judging units having further possible reasons is able to develop correspondingly next order analysis judging units. The order number of the analysis judging units corresponding to the analysis items 111, 112, 113 is able to set according to the theories of psychology or to add or delete according to actual observation. Furthermore, the analysis items 111, 112, 113 and the analysis judging units develop into a hierarchical tree structure. The preliminary results corresponding to the latest order analysis judging units in the hierarchical tree structure are the possible situations (or reasons) causing the corresponding analysis items; wherein, each of the latest order analysis judging unit corresponds to at least one of the preliminary results. According to the possibility of the latest order analysis judging unit, weighted scores are provided correspondingly to the preliminary results. For example, the second-order analysis judging units a1, a2 are the latest analysis judging units corresponding to the analysis item 111; wherein, the second-order analysis judging unit a1 has higher possibility, so the weighted score of the corresponding preliminary result D11 is higher; the second-order analysis judging unit a2 has lower possibility, so the weighted score of the corresponding preliminary result D12 is lower.

If the analysis item 111 is "to refuse food when mealtime", the development of the corresponding analysis judging units is described as follows: one first-order analysis judging unit 1111 would be "being full"; another first-order analysis judging unit 1112 would be "to throw a tantrum". The first-order analysis judging unit 1111 includes one second-order analysis judging unit a1 which shows "ate too much snack" and another second-order analysis judging unit a2 which shows "fed food already", while the first-order analysis judging unit 1112 do not have a corresponding second-order analysis judging unit. The analysis item 111 corresponds to all of the latest order analysis judging unit including the second order analysis judging units a1, a2 and the first order analysis judging unit 1112, etc. These latest order analysis judging units generate corresponding preliminary results. For example, the second order analysis judging unit a1 has two corresponding preliminary results, including "over indulgence" ID11 and "permissive parenting" ID12. The second order analysis judging unit a2 has one corresponding preliminary result which is "inconsistent parenting" ID13. The first order analysis judging unit 1112 has two corresponding preliminary results, including "poor emotional regulation ability (lack of emotional education)" ID14 and "poor conflict resolution ability" ID15. The description content of the latest order analysis judging units can be directly equal to the description content of the corresponding preliminary results.

Hereby, when a user selects the analysis item 1111 "to refuse food when mealtime", the analysis database 122 generates multiple preliminary results according to the analysis results of the analysis judging units in different orders. The analysis item 111 generates a plurality of preliminary results, so called a preliminary result group ID1. In the embodiment, the preliminary result group ID1 includes a plurality of preliminary results ID11, ID12, ID13, ID14, ID15, each of which has the corresponding description content, such as "over indulgence" ID11 ' "permissive parenting" ID12 ' "inconsistent parenting" ID13 ' "poor emotional regulation ability (lack of emotional education)" ID14 ' "poor conflict resolution ability" ID15. Similarly, the analysis database 122 generates preliminary result groups ID2, ID3 according to the analysis judging units of the analysis items 112, 113 in different orders. The preliminary result group ID2 includes a plurality of preliminary results ID21, ID22, ID23, ID24, each of which has the corresponding description content, such as "permissive parenting" ID21 ' "over indulgence" ID22 ' "permissive parenting" ID23 ' "western education" ID24. The preliminary result group ID3 includes a plurality of preliminary results ID31, ID32, ID33, each of which has the corresponding description content, such as "over indulgence" ID31 ' "over indulgence" ID32 ' "over indulgence" ID33. Therefore, when multiple analysis items 111, 112, 113 are selected, the operation processor 121 applies the preliminary results corresponding to the selected analysis items and executes an operation process to generate a final judgment result FS.

Figure 3:
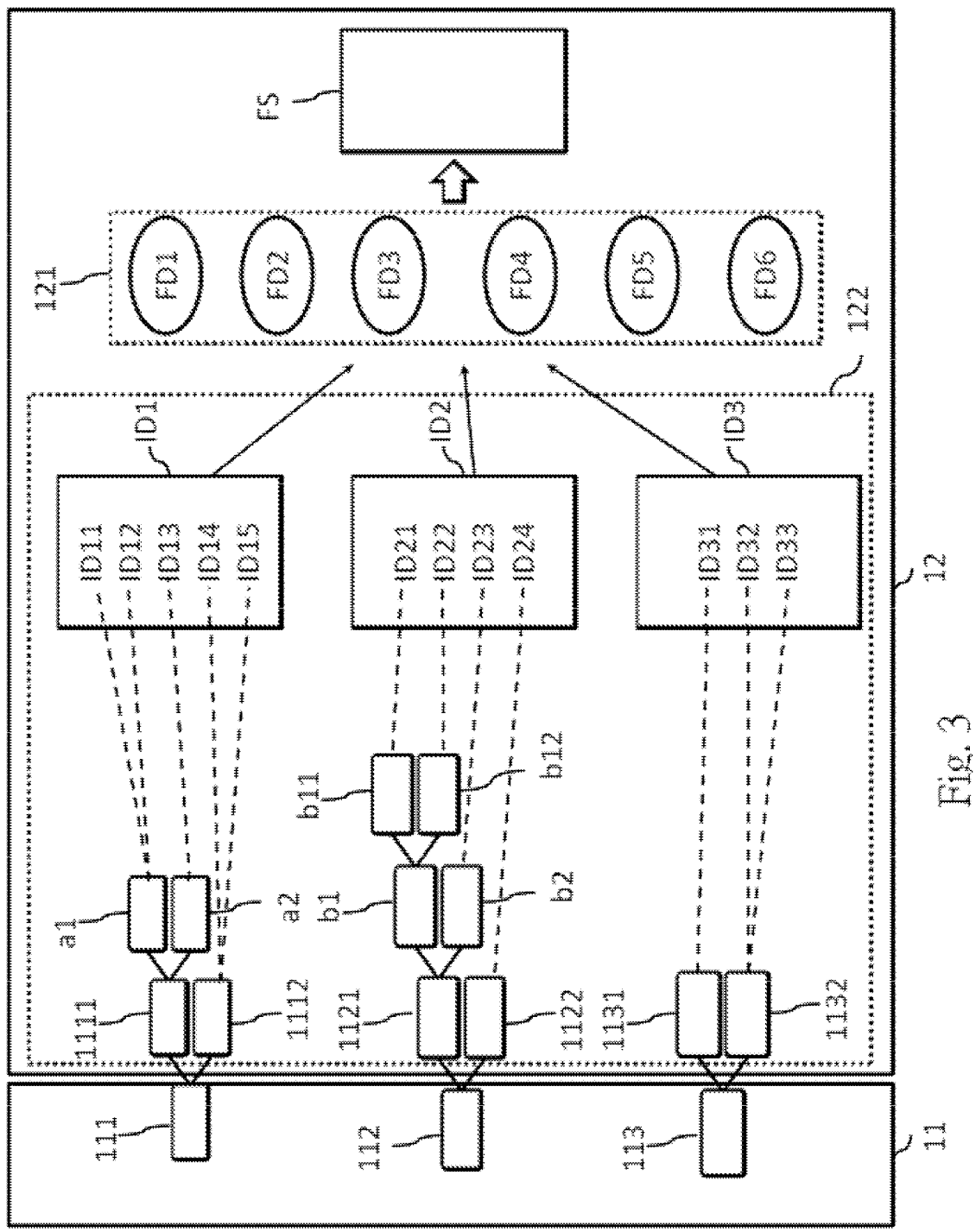
FIG. 3 is a schematic view of the relationship between the internal hierarchy and operation process in a determination module in another embodiment according to the system of the invention.
Figure 4:
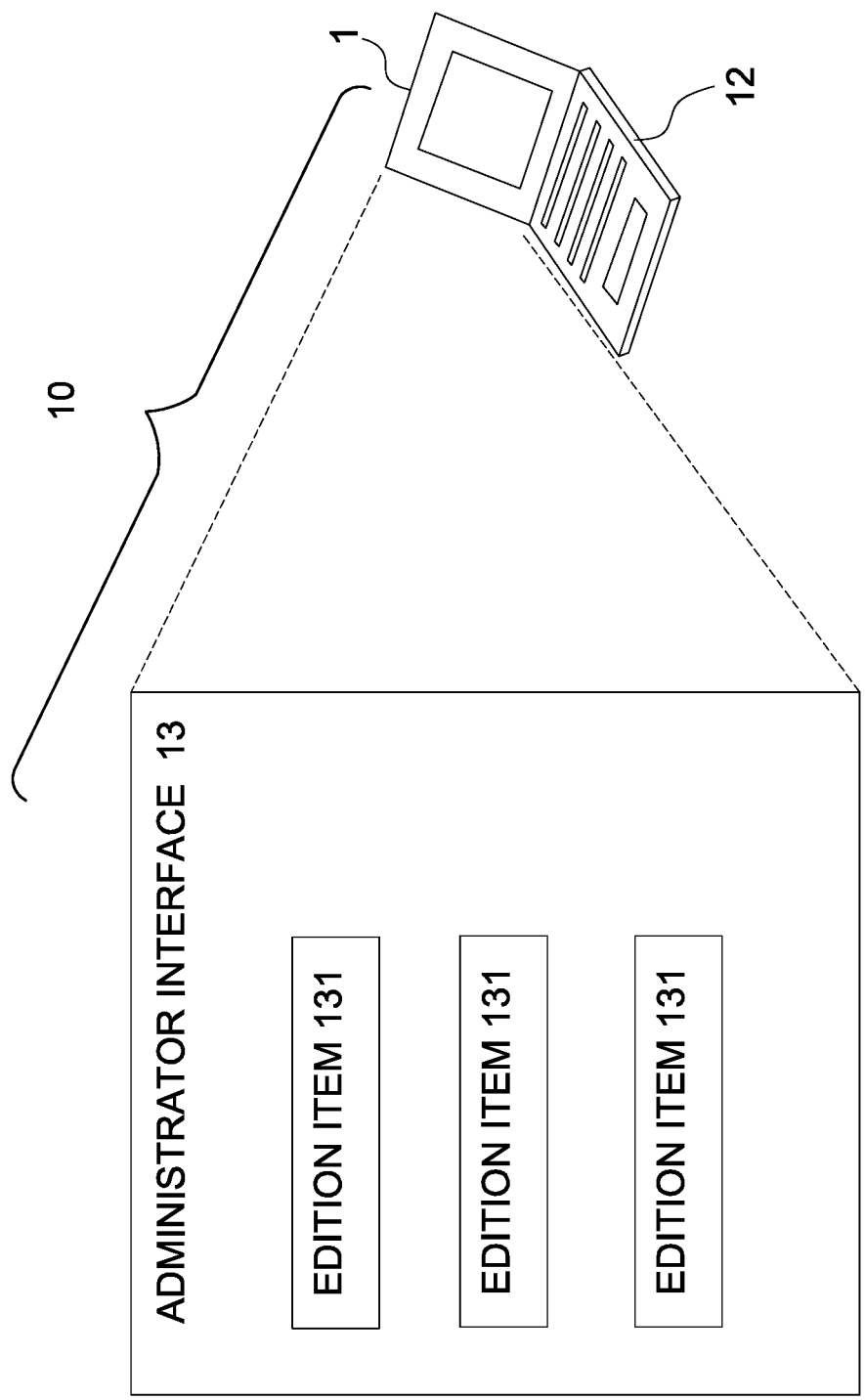
FIG. 4 is a schematic view of the operation screen of an administrator interface in an embodiment according to the system of the invention.

The invention has numerous ways to execute the operation process. In one embodiment, referring to FIG. 3, during the operation process, each of the preliminary results in the preliminary result groups ID1, ID2, ID3 includes a weighted score and a judgment group correspondingly. The weighted score defines the possibility of each of the preliminary results. The preliminary results with higher weighted score have higher possibilities, i.e. the preliminary result more possibly causes the behavior of the analysis item. The operation process adds the weighted scores of the preliminary results in the same judgment group together and obtains a total weighted score. When there is only one corresponding preliminary result in a judgment group, the weighted score of the preliminary result is the total weighted score of the judgment group. After calculating the total weighted scores of the judgment groups, the operation process ranks the judgment groups by the corresponding total weighted scores. For example, the preliminary results in the preliminary result group ID1 of the analysis item 111 include the preliminary result ID11, the preliminary result ID12, the preliminary result ID13, the preliminary result ID14, and the preliminary result ID15. The weighted score of the preliminary result ID11 is 6, and the preliminary result ID11 corresponds to a first judgment group FD1. The weighted score of the preliminary result ID12 is 3, and the preliminary result ID12 corresponds to a second judgment group FD2. The weighted score of the preliminary result ID13 is 4, and the preliminary result ID13 corresponds to a third judgment group FD3. The weighted score of the preliminary result ID14 is 2, and the preliminary result ID14 corresponds to a forth judgment group FD4. The weighted score of the preliminary result ID15 is 1, and the preliminary result ID15 corresponds to a fifth judgment group FD5. The preliminary results in the preliminary result group ID2 of the analysis item 112 include the preliminary result ID21, the preliminary result ID22, the preliminary result ID23, and the preliminary result ID24. The weighted score of the preliminary result ID21 is 5, and the preliminary result ID21 corresponds to the second judgment group FD2. The weighted score of the preliminary result ID22 is 3, and the preliminary result ID22 corresponds to the first judgment group FD1. The weighted score of the preliminary result ID23 is 5, and the preliminary result ID23 corresponds to the second judgment group FD2. The weighted score of the preliminary result ID24 is 3, and the preliminary result ID24 corresponds to a sixth judgment group FD6. The preliminary results in the preliminary result group ID3 of the analysis item 113 include the preliminary result ID31, the preliminary result ID32, and the preliminary result ID33. The weighted score of the preliminary result ID31 is 5, and the preliminary result ID31 corresponds to the second judgment group FD1. The weighted score of the preliminary result ID32 is 3, and the preliminary results ID32 corresponds to the first judgment group FD1. The weighted score of the preliminary result ID33 is 1, and the preliminary result ID33 corresponds to the first judgment group FD1. Each of the judgment groups respectively has an attribute defining whether two of them conflict with each other. In the operation process of the embodiment, the first judgment group FD1 and the second judgment group FD2 are set to conflict with each other.

During the operation process of the embodiment, if a user selects all the analysis items 111, 112,113, because all the preliminary results ID11, ID22, ID31, ID32, ID33 correspond to the first judgment group FD1, the weighted scores of the five preliminary results ID11, ID22, ID31, ID32, ID33 are added together and the total weighted score of the first judgment group FD1 is 18. Because the preliminary results ID12, ID21, ID23 correspond to the second judgment group FD2, the weighted scores of the three preliminary results ID12, ID21, ID23 are added together and the total weighted score of the second judgment group FD2 is 13. Because only the preliminary result ID13 corresponds to the third judgment group FD3, the total weighted score of the preliminary result ID13 is 4 and the total weighted score of the third judgment group FD3 is 4 which is equal to the total weighted score of the preliminary result ID13. Because the preliminary result ID14 corresponds to the forth judgment group FD4, the total weighted score of the preliminary result ID14 is 2 and the total weighted score of the forth judgment group FD4 is 2. Because the preliminary result ID15 corresponds to the fifth judgment group FD5, the total weighted score of the preliminary result ID15 is 1 and the total weighted score of the fifth judgment group FD5 is 1. Because the preliminary result ID16 corresponds to the sixth judgment group FD6, the total weighted score of the preliminary result ID16 is 3 and the total weighted score of the sixth judgment group FD6 is 3. The operation process ranks the judgment groups FD1, FD2, FD3, FD4, FD5, FD6 by the corresponding total weighted scores from high score to low score as follows: the first judgment group FD1 (whose total weighted score is 18), the second judgment group FD2 (whose total weighted score is 13), the third judgment group FD3 (whose total weighted score is 4), the sixth judgment group FD6 (whose total weighted score is 3), the forth judgment group FD4 (whose total weighted score is 2), the fifth judgment group FD5 (whose total weighted score is 1). In another embodiment, the operation process does not rank the judgment groups, but judges whether the attributes of any two judgment groups conflict with each other. There are two patterns to process each of two judgment groups conflicting with each other. The first pattern is that the operation process obtains difference between two total weighted scores of judgment groups which conflict with each other, renews the total weighted score of the judgment group with the higher weighted score according to the difference, removes the judgment group with the lower weighted score, and ranks the remaining judgment groups by the corresponding total weighted scores. For example, the first judgment group FD1 (whose total weighted score is 18) and the second judgment group FD2 (whose total weighted score is 13) conflict with each other, and the difference between the total weighted scores of the first judgment group FD1 and the second judgment group FD2 is 5. Because the total weighted score of the first judgment group FD1 is higher than the total weighted score of the second judgment group FD2, the total weighted score of the first judgment group FD1 is renewed as 5. Then the operation process removes the second judgment group which has the lower weighted score and ranks the remaining judgment groups FD1, FD3, FD4, FD5, FD6 by the corresponding total weighted scores. The rank result according to the total weighted scores from high score to low score is the first judgment group FD1 (the renewed total weighted score is 5), the third judgment group FD 3 (the total weighted score is 4), the sixth judgment group FD6 (the total weighted score is 3), the forth judgment group FD4 (the total weighted score is 2), the fifth judgment group FD5 (the total weighted score is 1). The second pattern is that the operation process removes the judgment group with lower total weighted score from the judgment groups which conflict with each other, and ranks the remaining judgment groups by the corresponding total weighted scores. For example, the first judgment group FD1 (whose total weighted score is 18) and the second judgment group FD2 (whose total weighted score is 13) conflict with each other. Because the total weighted score of the second judgment group FD2 is lower than the total weighted score of the first judgment group FD1, the operation process removes the second judgment group, and ranks the remaining judgment groups FD1, FD3, FD4, FD5, FD6 by the corresponding total weighted scores. The rank result according to the total weighted scores is the first judgment group FD1 (whose total weighted score is 18), the third judgment group FD 3 (whose total weighted score is 4), the sixth judgment group FD6 (whose total weighted score is 3), the forth judgment group FD4 (whose total weighted score is 2), the fifth judgment group FD5 (whose total weighted score is 1).

Each of the judgment groups has a corresponding explanation according to the content of the corresponding preliminary result(s). For example, the content of the preliminary results ID11, ID22, ID31, ID32, ID33 is "over indulgence", so the first judgment group has a explanation as "over indulgence". The final judgment result FS shows an analysis result reference for a user on the user interface according to the foregoing ranking result and the corresponding explanations. For example, the possibility of the corresponding explanations according to the foregoing ranking result from high to low is "over indulgence", "inconsistent parenting", "western education", "poor emotional regulation ability (lack of emotional education)" and "poor conflict resolution ability". The final judgment result FS can only show the top explanations of the judgment groups and further provides more detailed explanations or treatment suggestions.

In the embodiment, the administrator interface 13 includes a plurality of edition items 131 for editing the analysis items, at least one of the preliminary results corresponding to each of the analysis items, each of the weighted scores corresponding to each of the preliminary results, each of the judgment groups corresponding to at least one of the preliminary results, and each of the attributes corresponding to each of the judgment groups. The attributes define whether two of the preliminary results can be added together or conflict with each other. In addition, the edition items 131 apply to edit at least one of the analysis judging units corresponding to each of the analysis items. The analysis judging unit correspondingly connects to at least one of the preliminary results through a hierarchical structure. The analysis judging unit might be a one-level hierarchical structure or a multiple level hierarchical structure. Each of the hierarchical structures is the relationship diagram of all causes which is developed from each of the analysis items by analyzing the relationships between the levels of each of the hierarchical structures or the relationships between the level (s) of each of the hierarchical structures and each of the analysis items according to expert's professional knowledge and experience. The development order of the level (s) of each of the hierarchical structures is based on the level of causes, the level of details, or the relation between causes and effects. Experts can edit, add, or delete the column (s) or level (s) of each of the analysis judging units and input corresponding analysis content into the columns of the analysis judging units by themselves. After experts edit the edition item (s) 131 by the administrator interface 13, the analysis items, the preliminary results, the weighted scores, the judgment groups, the attributes and/or the analysis judging units are saved into the user interface 11 or the determination module 12. The operation process executes further analysis according to the edition version of the analysis items, the preliminary results, the weighted scores, the judgment groups, the attributes and/or the analysis judging units.

In another embodiment of the invention, during the operation process, each of the preliminary results of the preliminary result groups ID1, ID2, ID3 includes a weighted score and an attribute correspondingly. The weighted score defines the possibility of each of the preliminary results. The attribute defines whether two of the preliminary results can be added together. The operation process obtains a total value by adding the weighted scores of the preliminary results that can be added together, renews the higher weighted score of the preliminary result according to the total value, and removes the preliminary result with the lower weighted score. For example, the preliminary result group ID1 of the analysis item 111 has the preliminary results ID11, ID12, ID13, ID14, ID15. The weighted score of the preliminary result ID11 is 6. The weighted score of the preliminary result ID12 is 3. The weighted score of the preliminary result ID13 is 4. The weighted score of the preliminary result ID14 is 2. The weighted score of the preliminary result ID15 is 1. The preliminary result group ID2 of the analysis item 112 has the preliminary results ID21, ID22, ID23, ID24. The weighted score of the preliminary result ID21 is 5. The weighted score of the preliminary result ID22 is 3. The weighted score of the preliminary result ID23 is 5. The weighted score of the preliminary result ID24 is 3. The preliminary result group ID3 of the analysis item 113 has the preliminary results ID31, ID32, ID33. The weighted score of the preliminary result ID31 is 5. The weighted score of the preliminary results ID32 is 3. The weighted score of the preliminary results ID33 is 1. In the operation process, the attributes of the preliminary results ID11, ID22, ID31, ID32, ID33 are defined that they can be added together, and the attributes of the preliminary results ID12, ID21, ID23 are defined that they can be added together.

During the operation process of the embodiment, if a user selects all the analysis items 111, 112,113, the preliminary results of the selected analysis items 111, 112, 113 which correspond to the same or similar contents have the attributes to define that they can be added together. Therefore, the contents of the preliminary results ID11, ID22, ID31, ID32, ID33 are all "over indulgence", and the attributes of the preliminary results ID11, ID22, ID31, ID32, ID33 define that they can be added together. The weighted scores of the five preliminary results ID11, ID22, ID31, ID32, ID33 are added together to obtain a total value 18. Because the weighted score of the preliminary result ID11 is higher, it is renewed from 6 to 18 according the total value and the preliminary results ID22, ID31, ID32, ID33 with lower weighted scores are removed. Besides, the preliminary results ID12, ID21, ID23 have the same content "permissive parenting" and their attributes are defined that they can be added together. The weighted scores of the three preliminary results ID12, ID21, ID23 are added together to obtain a total value 13. Because both the weighted scores of the preliminary results ID21, ID23 are the same higher weighted scores, each of them could be chosen as representative. If the preliminary result ID21 is chosen, its weighted score is renewed from 5 to 13 according to the total value and the preliminary results ID12, ID23 are removed. As to the other preliminary results ID13, ID24, ID14, ID15, their attributes are not defined that they can be added together, so they do not need to be added together. The operation process ranks the preliminary results according to the weighted scores from high score to low score as follows: the preliminary result ID11 (whose renewed weighted score is 18), the preliminary result ID21 (whose renewed weighted score is 13), the preliminary result ID13 (whose weighted score is 4), the preliminary result ID24 (whose weighted score is 3), the preliminary result ID14 (whose weighted score is 2), the preliminary result ID15 (whose weighted score is 1). The final judgment result FS ranks the corresponding contents according to the foregoing ranking result of the preliminary results and shows on the user interface to provide a user the analysis result reference. For example, the possibility of the corresponding explanations according to the foregoing ranking result from high to low is "over indulgence", "permissive parenting", "inconsistent parenting", "western education", "poor emotional regulation ability (lack of emotional education)" and "poor conflict resolution ability". The final judgment result FS can only show the top explanations of the preliminary results and further provides more detailed explanations or treatment suggestions.

In another embodiment of the operation process of the invention according to the previous embodiment, the attributes of the preliminary results in the preliminary result groups ID1, ID2, ID3 of the analysis items 111, 112, 113 further define whether two of the preliminary results conflict with each other. There are two patterns when two preliminary results conflict with each other. The first pattern is that the weighted scores of the preliminary results are subtracted from each other according to the attributes of the preliminary results. For example, based on the remaining preliminary results of the previous embodiment, the attributes of the preliminary result ID11 "over indulgence" and the preliminary result ID21 "permissive parenting" are defined that the two preliminary results ID11, ID21 conflict with each other. The operation process obtains a difference between the preliminary result ID 11 "over indulgence" (the renewed weighted score is 18) and the preliminary result ID21 "permissive parenting" (the renewed weighted score is 13), and the difference is 5. Because the weighted score of the preliminary result ID11 is higher than the weighted score of the preliminary result ID21, the weighted score of the preliminary result ID11 is renewed to 5 according to the difference, and the preliminary result ID21 with the lower weighted score is removed. The operation process ranks the remaining preliminary results according to the rank of the newest weighted scores of the remaining preliminary results from high score to low score are shown as follows: the preliminary result ID11 (whose renewed weighted score is 5), the preliminary result ID13 (whose weighted score is 4), the preliminary result ID24 (whose weighted score is 3), the preliminary result ID14 (whose weighted score is 2), the preliminary result ID15 (whose weighted score is 1). The second pattern is that the operation process removes the preliminary result with the lower weighted score that their corresponding preliminary results conflict with each other and ranks the remaining preliminary results by the corresponding weighted scores. For example, the preliminary result ID11 "over indulgence" (the renewed weighted score is 18) and the preliminary result ID21 "permissive parenting" (the renewed weighted score is 13) conflict with each other, so the preliminary result ID21 with lower weighted score is removed. Furthermore, the operation process ranks the remaining preliminary results according to the rank of the newest weighted scores of the remaining preliminary results from high score to low score are shown as follows: the preliminary result ID11 (whose renewed weighted score is 18), the preliminary result ID13 (whose weighted score is 4), the preliminary result ID24 (whose weighted score is 3), the preliminary result ID14 (whose weighted score is 2), the preliminary result ID15 (whose weighted score is 1). Similarly, the final judgment result FS ranks the corresponding contents according to the preliminary results and shows on the user interface to provide a user the analysis result reference. For example, the possibility of the corresponding explanations according to the foregoing ranking result from high to low is "over indulgence", "inconsistent parenting", "western education", "poor emotional regulation ability (lack of emotional education)" and "poor conflict resolution ability". The final judgment result FS can only show the top explanations of the preliminary results and further provides more detailed explanations or treatment suggestions.

In the embodiment, the administrator interface 13 includes a plurality of edition items 131 for editing the analysis items, at least one of the preliminary results corresponding to each of the analysis items, each of the weighted scores corresponding to each of the preliminary results, and each of the attributes corresponding to each of the judgment groups. The attributes define whether two of the preliminary results can be added together or conflict with each other. In addition, the edition items 131 apply to edit at least one of the analysis judging units corresponding to each of the analysis items. The analysis judging unit correspondingly connects to at least one of the preliminary results through a hierarchical structure. The analysis judging unit might be a one-level hierarchical structure or a multiple level hierarchical structure. Each of the hierarchical structures is the relationship diagram of all causes which is developed from each of the analysis items by analyzing the relationships between the levels of each of the hierarchical structures or the relationships between the level (s) of each of the hierarchical structures and each of the analysis items according to expert's professional knowledge and experience. The development order of the level (s) of each of the hierarchical structures is based on the level of causes, the level of details, or the relation between causes and effects. Experts can edit, add, or delete the column (s) or level (s) of each of the analysis judging units and input corresponding analysis content into the columns of the analysis judging units by themselves. After experts edit the edition item (s) 131 by the administrator interface 13, the analysis items, the preliminary results, the weighted scores, the judgment groups, the attributes and/or the analysis judging units are saved into the user interface 11 or the determination module 12. The operation process executes further analysis according to the edited version of the analysis items, the preliminary results, the weighted scores, the judgment groups, the attributes and/or the analysis judging units.

In another embodiment of the operation process, the preliminary results in the preliminary result groups ID1, ID2, ID3 of the analysis item 111, 112, 113 do not have corresponding weighted scores, and the operation process counts and ranks the preliminary results according to the frequency of occurrence the preliminary results with the same content. In this embodiment, the weighted scores of the preliminary results could be viewed as 1.

Figure 6:
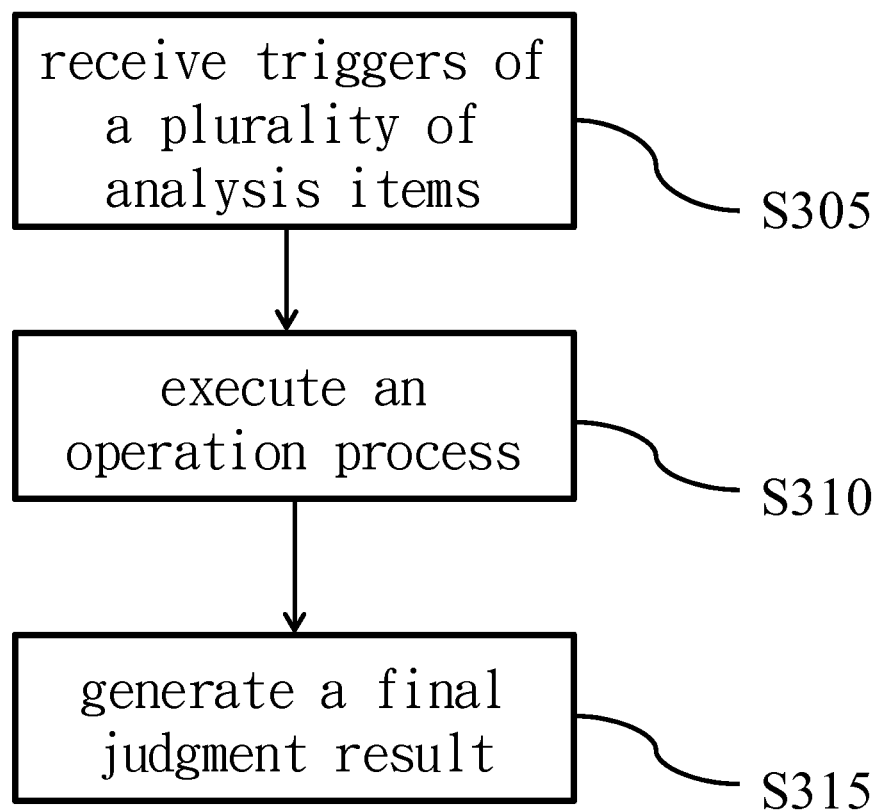
FIG. 6 is a process flowchart of an embodiment according to the method of the invention.

FIG. 6 is a process flowchart of an embodiment according to the method of the invention. In FIG. 6, also referring to FIGS. 1 to 4, the method of the invention includes the step of receiving a plurality of triggers of the analysis items 111, 112, 113, each of which corresponds at least one of preset preliminary results (step S305). In the embodiment, after a user selects a plurality of the analysis items 111, 112, 113 of the user interface 11, the analysis judging units of the analysis database 122 are started and the corresponding preliminary results of the analysis items 111, 112, 113 are obtained.

The method of the invention further has the step of executing an operation process (step S310) to generate a final judgment result FS according to a plurality of the preliminary results of the triggered analysis items 111, 112, 113 (step S315). In the embodiment, the number of the analysis items selected can be one, more than 3 (more preferably), or 5 (the most preferably) to provide a more accurate analysis judgment.

Figure 7:
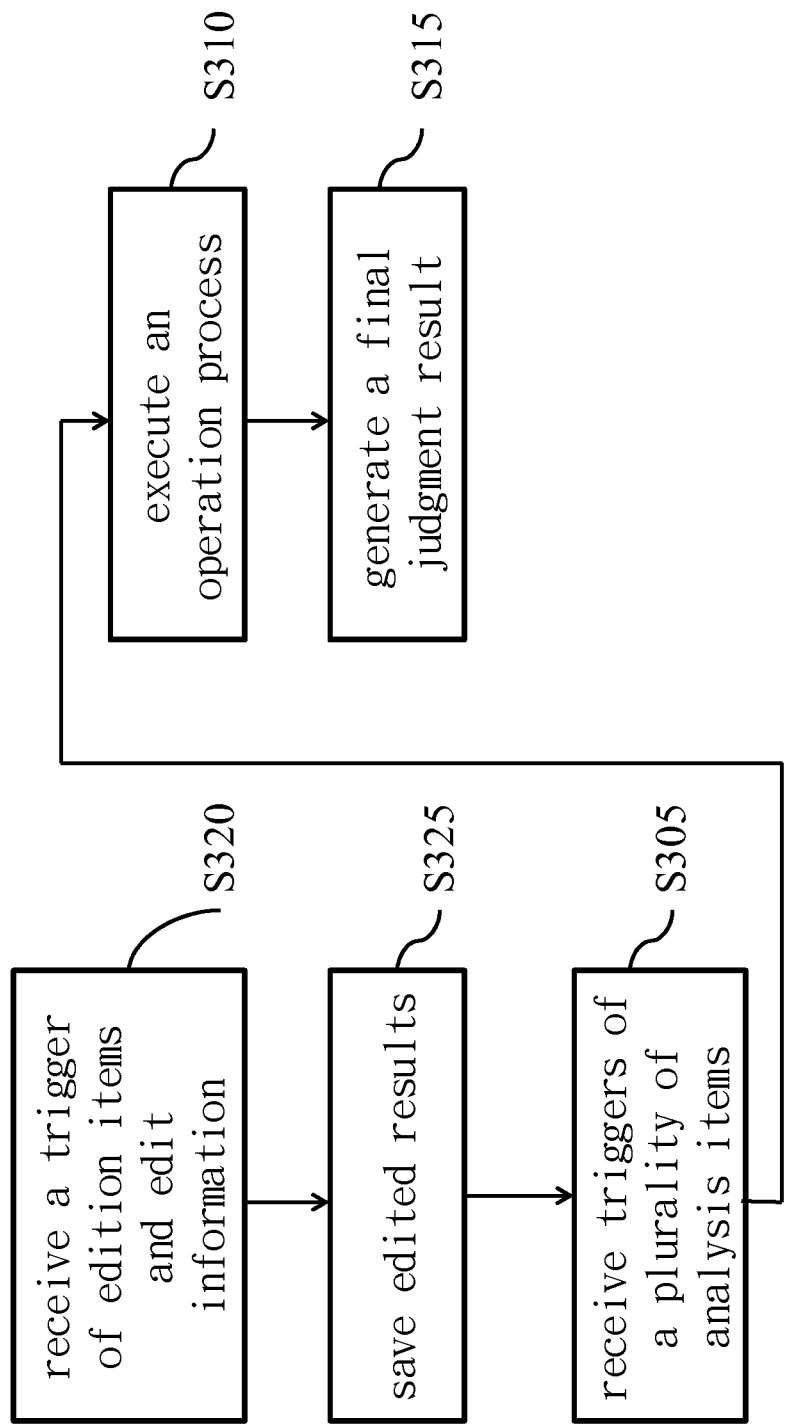
FIG. 7 is another process flowchart of an embodiment according to the method of the invention.

Additionally, referring to FIG. 7, before receiving triggers of a plurality of analysis items (step S305), the method of the invention further includes the step of receiving a trigger of at least one of edition items and obtaining editing information to edit each of the corresponding analysis items or each of the corresponding preliminary results (step S320), and saving each of the edited analysis items or each of the edited preliminary results (step S325). After the step S325, the method of the invention can start the following steps, including receiving triggers of a plurality of analysis items (step S305), executing the operation process (step S310) and generating a final judgment result (step S315). Furthermore, the weighted scores, the judgment groups, the attributes and the analysis judging units can also be edited by the administrator interface 13 and saved, and then the final judgment result FS can be generated by the steps S310, S315, S320.

In conclusion, the invention provides the auxiliary analysis system using expert information and the method thereof which apply the operation processor 121 to perform the weight calculation according to the frequency, numeric values and attributes of preliminary results corresponding to the analysis items selected by a user to obtain more objective, more accurate and logical analysis judgments. After analyzing with the auxiliary analysis system using expert information and the method thereof, users can understand the reasons behind events observed correctly in a short period and get the suggestions for revising the follow-up operation means to enhance efficiency. Experts can accumulate and revise their professional knowledge continuously according to continuous observations and users' feedback to improve accuracy and reliability of analysis results. The auxiliary analysis system using expert information and the method thereof do not limit to the application of child psychology. Any fields of using expert information and analyzing comprehensively by observation of concrete facts can be included.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the invention have been described with reference to the figures, it will be understood by those of ordinary skill in the art that various changes in form and details may be made therein without departing from the spirit and scope of the invention as defined by the following claims.

What is claimed is:

1. An auxiliary analysis system, adapted for performing a psychoanalysis to a first user by using expert information, comprising:
    a display;
    an analysis database, is configured to record a plurality of analysis items, and a plurality of preliminary result groups respectively corresponding to the plurality of analysis items;
    wherein each of the preliminary result groups comprises one or more preliminary results, wherein the analysis database is further configured to record a weighted score of each of the one or more preliminary results in each of the preliminary result groups,
    wherein the analysis items respectively indicate a plurality of concrete behaviors, wherein the concrete behaviors are preset according to professional books or the expert information related to the psychoanalysis,
    wherein each of the one or more preliminary results of one preliminary result group indicate a reason causing one of the concrete behaviors indicated by one analysis item corresponding to that said one preliminary result group,
    wherein a possibility of the reason causing that said one of the concrete behaviors is indicated by the weighted score of that said one of the one or more preliminary results,
    wherein the weighted scores of all the one or more preliminary results, and connection relationships between the analysis items and the corresponding one or more preliminary results are predetermined according to the professional books or the expert information related to the psychoanalysis,
    a processor, coupled to the display and the analysis database, is configured to show a user interface including the analysis items on the display,
    wherein in response to one or more target analysis items among the analysis items are triggered by a selection performed by a second user, the processor is further configured to identify one or more target preliminary result groups respectively corresponding to the one or more target analysis items among the preliminary result groups according to the analysis database, wherein one or more observed behaviors of the first user are one or more target concrete behaviors indicated by the one or more target analysis items,
    wherein the processor is further configured to group a plurality of target preliminary results of the one or more target preliminary result groups into a plurality of judgement groups according to a plurality of target reasons indicated by the plurality of target preliminary results, wherein one or more first target preliminary results in the same one of the judgement groups indicate the same one of the target reasons,
    wherein the processor is further configured to calculate a total weighted score of each of the judgement groups according to the weighted scores of the target preliminary results grouped in each of the judgement groups,
    wherein the processor is further configured to rank the judgement groups, from highest to lowest, according to the total weighted scores of the judgement groups,
    wherein the processor is further configured to generate a final judgement result by the ranked judgement groups and show the final judgement result in the user interface on the display, wherein the final judgement result indicates the one or more most possible reasons causing the one or more observed behaviors of the first user, so as to complete the psychoanalysis to the first user.

2. The system, as recited in claim 1, wherein in the operation of calculating a total weighted score of each of the plurality of judgement groups according to the weighted scores of the target preliminary results grouped in each of the plurality of judgement groups,
    regarding one of the plurality of judgement groups, the processor sums the weighted scores of the target preliminary results in that said one of judgment groups to obtain a summation as the total weighted score of that said one of the plurality of judgement groups, so as to obtain the total weighted score of each of the plurality of judgement groups.

3. The system, as recited in claim 1, wherein a detailed explanation of the one or more observed behaviors of the first user is provided by the final judgement result, or the final judgement result is further used as references for treatment suggestions regarding the first user.

4. The system, as recited in claim 2, wherein each of the judgment groups respectively has an attribute,
    wherein the processor determines whether two of the judgment groups conflict with each other according to the attributes of that said two of the judgment groups,
    wherein in response to determining that two of the judgment groups conflict with each other, the processor obtains a difference between the total weighted scores of that said two of the judgment groups conflicting with each other,
    wherein the processor renews the total weighted score of the judgment group with the higher weighted score among that said two of the judgment groups according to the difference, removes the judgment group with the lower weighted score among that said two of the judgment groups, and ranks the remaining judgment groups again according to the corresponding total weighted scores.

5. The system, as recited in claim 2, wherein each of the judgment groups respectively has an attribute,
    wherein the processor determines whether two of the judgment groups conflict with each other according to the attributes of that said two of the judgment groups,
    wherein in response to determining that two of the judgment groups conflict with each other, the processor removes the judgment group with lower total weighted score among that two of the judgment groups from the judgment groups, and ranks the remaining judgment groups again according to the corresponding total weighted scores.

6. The system, as recited in claim 1, wherein in the analysis database,
    the connection relationships between the one or more preliminary results of one of the preliminary result groups corresponding to one of the analysis items is recorded through a hierarchical tree structure corresponding to that said one of the analysis items,
    wherein the hierarchical tree structure has a root layer and one or more judging layers, wherein that said one of the analysis items is in the root layer, and the one or more preliminary results corresponding to that said one of the analysis items are in the last one of the one or more judging layers of the hierarchical tree structure corresponding to that said one of the analysis items.

7. The system, as recited in claim 1, wherein
the processor further comprising shows an administrator interface corresponding to the user interface,
wherein the administrator interface including a plurality of edition items for editing the analysis items, the one or more preliminary results corresponding to each of the analysis items, and the weighted scores of each of the one or more preliminary results corresponding to each of the analysis items.

8. The system, as recited in claim 4, wherein
the processor further shows an administrator interface corresponding to the user interface,
wherein the administrator interface including a plurality of edition items for editing the analysis items, the one or more preliminary results corresponding to each of the analysis items, the weighted scores of each of the one or more preliminary results corresponding to each of the analysis items, each of the judgment groups corresponding to each of the one or more preliminary results corresponding to each of the analysis items, and the attributes corresponding to each of the judgment groups.

9. The system, as recited in claim 5, wherein
the processor further shows an administrator interface corresponding to the user interface,
wherein the administrator interface including a plurality of edition items for editing the analysis item, the one or more preliminary results corresponding to each of the analysis items, and the weighted scores of each of the one or more preliminary results corresponding to each of the analysis items.

10. The system, as recited in claim 6, wherein
the processor further shows an administrator interface corresponding to the user interface,
wherein the administrator interface including a plurality of edition items for editing the analysis items, the one or more preliminary results corresponding to each of the analysis items, the weighted scores of each of the preliminary results, and connection relationships between all the nodes of the hierarchical tree structure.

11. An auxiliary analysis method, adapted for an auxiliary analysis system performing a psychoanalysis to a first user by using expert information, the method comprising the steps of:
showing a user interface including a plurality of analysis items on a display of the auxiliary analysis system according to an analysis database of the auxiliary analysis system, wherein the analysis database records the plurality of analysis items, and a plurality of preliminary result groups respectively corresponding to the plurality of analysis items,
wherein each of the preliminary result groups comprises one or more preliminary results, wherein the analysis database further records a weighted score of each of the one or more preliminary results in each of the preliminary result groups,
wherein the analysis items respectively indicate a plurality of concrete behaviors, wherein the concrete behaviors are preset according to professional books or the expert information related to the psychoanalysis,
wherein each of the preliminary results of one preliminary result group indicate a reason causing one of the concrete behaviors which is indicated by one analysis item corresponding to that said one preliminary result group,
wherein a possibility of the reason causing that said one of the concrete behaviors is indicated by the weighted score of that said one of the preliminary results,
wherein the weighted scores of all the preliminary results, and connection relationships between the analysis items and the corresponding preliminary results are predetermined according to the professional books or the expert information related to the psychoanalysis,
in response to one or more target analysis items among the analysis items are triggered by a selection performed by a second user, identifying one or more target preliminary result groups respectively corresponding to the one or more target analysis items among the preliminary result groups according to the analysis database, wherein one or more observed behaviors of the first user are one or more target concrete behaviors indicated by the one or more target analysis items;
grouping a plurality of target preliminary results of the one or more target preliminary result groups into a plurality of judgement groups according to a plurality of target reasons indicated by the plurality of target preliminary results, wherein one or more first target preliminary results in the same one of the judgement groups indicate the same one of the target reasons;
calculating a total weighted score of each of the judgement groups according to the weighted scores of the plurality of target preliminary results grouped in each of the judgement groups;
ranking the judgement groups, from highest to lowest, according to the total weighted scores of the judgement groups;
generating a final judgement result by the ranked judgement groups and show the final judgement result in the user interface on the display, wherein the final judgement result indicates the one or more most possible reasons causing the one or more observed behaviors of the first user, so as to complete the psychoanalysis to the first user.

12. The method, as recited in claim 11, further comprising the steps of:
in response to at least one edition item is triggered, obtaining editing information corresponding to the at least one edition item for editing one of the corresponding analysis item, the corresponding preliminary results, and the weighted scores of each of the corresponding preliminary results; and saving the edited analysis item, the edited preliminary results and the edited weighted scores respectively.

13. An auxiliary analysis system, adapted for performing a psychoanalysis to a first user by using expert information, comprising:
a display;
an analysis database, is configured to record a plurality of analysis items, and a plurality of preliminary result groups respectively corresponding to the plurality of analysis items;
wherein each of the preliminary result groups comprises one or more preliminary results, wherein the analysis database is further configured to record an attribute and a weighted score of each of the one or more preliminary results in each of the preliminary result groups, wherein the analysis items respectively indicate a plurality of concrete behaviors, wherein the concrete behaviors are preset according to professional books or the expert information related to the psychoanalysis, wherein each of the one or more preliminary results of one preliminary result group indicate a reason causing one of the concrete behaviors indicated by one analysis item corresponding to that said one preliminary result group, wherein a possibility of the reason causing that said one of the concrete behaviors is indicated by the weighted score of that said one of the one or more preliminary results, wherein the attributes and the weighted scores of all the preliminary results, and connection relationships between the analysis items and the corresponding preliminary results are predetermined according to the professional books or the expert information related to the psychoanalysis, a processor, coupled to the display and the analysis database, is configured to show a user interface including the analysis items on the display, wherein in response to one or more target analysis items among the analysis items are triggered by a selection performed by a second user, the processor is further configured to identify one or more target preliminary result groups respectively corresponding to the one or more target analysis items among the plurality of preliminary result groups according to the analysis database, wherein one or more observed behaviors of the first user are one or more target concrete behaviors indicated by the one or more target analysis items, wherein the processor is further configured to merge two or more target preliminary results in the one or more target preliminary result groups as one merged target preliminary result according to the attributes of the two or more target preliminary results, wherein the attributes of the two or more target preliminary results indicates that the two or more target preliminary results are able to be merged together, wherein the merged target preliminary result is one target preliminary result having the highest weighted score among the two or more target preliminary results, wherein the processor is further configured to update the weighted score of the merged target preliminary result as a total value calculated by summing the weighted scores of all the two or more target preliminary results, wherein the processor is further configured to rank the remaining target preliminary results in the one or more target preliminary result groups, from highest to lowest, according to the corresponding weighted scores of the remaining target preliminary results, wherein the processor is further configured to generate a final judgement result by the ranked remaining target preliminary results and show the final judgement result in the user interface on the display, wherein the final judgement result indicates the one or more most possible reasons causing the one or more observed behaviors of the first user, so as to complete the psychoanalysis to the first user.

14. The system, as recited in claim 13, wherein the processor further shows an administrator interface corresponding to the user interface, wherein the administrator interface including a plurality of edition items for editing the analysis items, the one or more preliminary results corresponding to each of the analysis items, and the attributes and the weighted scores of each of the one or more preliminary results corresponding to each of the analysis items.

15. The system, as recited in claim 13, wherein in response to determining that the attributes of two further target preliminary results in the one or more target preliminary result groups are conflicting with each other, the processor calculate a difference value between the weighted scores of the two further target preliminary results, updates the weighted score of one of the two further target preliminary results having the higher weighted score as the difference value, removes another of the two further target preliminary results, and ranks the remaining target preliminary results in the one or more target preliminary result groups according to the weighted scores of the remaining target preliminary results.

16. The system, as recited in claim 13, wherein in response to determining that the attributes of two further target preliminary results in the one or more target preliminary result groups are conflicting with each other, the processor removes one of the two further target preliminary results having the lower weighted score, and ranks the remaining target preliminary results in the one or more target preliminary result groups according to the weighted scores of the remaining target preliminary results.

17. The system, as recited in claim 13, wherein a detailed explanation of the one or more observed behaviors of the first user is provided by the final judgement result, or the final judgement result is further used as references for treatment suggestions regarding the first user.

18. The system, as recited in claim 13, wherein in the analysis database, the connection relationships between the one or more preliminary results of one of the preliminary result groups corresponding to one of the analysis items is recorded through a hierarchical tree structure corresponding to that said one of the analysis items, wherein the hierarchical tree structure has a root layer and one or more judging layers, wherein that said one of the analysis items is in the root layer, and the one or more plurality of preliminary results corresponding to that said one of the analysis items are in the last one of the one or more judging layers of the hierarchical tree structure corresponding to that said one of the analysis items.

* * * * *